United States Patent [19]

Toohey

[11] Patent Number: 4,749,080

[45] Date of Patent: Jun. 7, 1988

[54] PACKAGED REUSABLE MOIST CLOTH AND METHOD

[76] Inventor: Richard D. Toohey, 140 Peace Acre La., Stratford, Conn. 06497

[21] Appl. No.: 109,457

[22] Filed: Oct. 16, 1987

[51] Int. Cl.$^4$ ............................................. B65D 85/67
[52] U.S. Cl. ....................................... 206/210; 53/425; 206/484; 206/494; 206/812
[58] Field of Search ................ 53/400, 425; 206/209, 206/210, 361, 438, 484, 494, 524.2, 812

[56] References Cited

U.S. PATENT DOCUMENTS

| | | | |
|---|---|---|---|
| 2,402,982 | 7/1946 | Steenbergen | 206/210 |
| 2,621,784 | 12/1952 | Van Boytham | 206/361 |
| 3,889,804 | 6/1975 | Ravich | 206/812 |
| 4,101,026 | 7/1978 | Bonk | 206/812 |
| 4,185,754 | 1/1980 | Julius | 206/210 |
| 4,220,244 | 9/1980 | Elmore | 206/812 |
| 4,624,101 | 11/1986 | Marchioni et al. | 53/425 |
| 4,651,874 | 3/1987 | Nakamura | 206/812 |

FOREIGN PATENT DOCUMENTS 1299826  12/1972  United Kingdom ................. 53/425

*Primary Examiner*—Jimmy G. Foster
*Attorney, Agent, or Firm*—Perman & Green

[57] ABSTRACT

Sterile package moist woven cloth towel and method for producing same in hermetically sealed packages. The invention comprises inserting a small woven cotton cloth towel, such as of terry cotton, into a liquid impervious envelope, injecting a sufficient volume of liquid into the envelope to impregnate the towel, hermetically sealing the envelope and finally exposing the envelope to sufficient radiation to cause sterilization of the liquid-impregnated towel therewithin. The woven cloth is capable of laundering for subsequent use in wet or dry condition.

10 Claims, No Drawings

PACKAGED REUSABLE MOIST CLOTH AND METHOD

BACKGROUND OF THE INVENTION

The present invention relates to the field of pre-moistened towels or towelettes conventionally-used for the cleaning of the hands or other body parts at locations remote from the home, such as in restaurants, in an automobile, in parks, restrooms, etc.

Prior known products of this type generally consist of one or more non-woven paper-type towels packaged within a sealed, sometimes-resealable envelope or package, which towels are impregnated with bacteria-resistant liquid compositions such as alcoholic solutions including oils, perfumes, embodiments, medicants and/or variety of other organic chemicals depending upon the intended use of the towels. Such paper towels have very little wet strength, cannot be laundered, and are intended to be used a single time and then disposed of. Thus, such products are commonly sold in resealable packets containing six or more moist paper towels labelled for a particular use such as for baby use, etc. While some such towels may be useful for several purposes, no such towels are suitable for all uses and some such towels can be physically harmful if used for an unintended purpose, i.e., by depositing chemicals which can irritate or infect certain body parts.

It is known that woven fabrics are stronger than non-woven fabrics such as felted paper and have excellent wet strength which adapts them for laundering and reuse. It is also known that cotton fabrics are highly absorbent of water, particularly terry cotton cloths, and have excellent softness and natural properties of purity which account for their use in dry condition in the medical field as gauze pads, bandages and other materials.

It is also known that water, particularly pure or distilled or natural spring water, is a universally-safe liquid for application to all body parts and is the most universal of all liquid solvents. However, non-sterile cotton fabrics, particularly when damp or moist, provide an ideal site for the deposit and growth of bacteria, even if the damp cotton fabric is sealed within an air-impervious package. Therefore, while woven cotton fabric and pure water are preferred materials for sanitary cleaning purposes, the combination of these materials is not available in a hermetically sealed, sterile package intended for future use in locations remote from the home.

SUMMARY OF THE INVENTION

The present invention relates to the discovery that woven cotton fabrics, moistened with aqueous compositions, are universally useful for a wide variety of body cleaning purposes, and that sanitary packages of such moistened cotton fabrics having excellent resistance to bacterial growth over extended periods of time can be produced by hermetically-sealing the moist woven cotton fabric within an air-impervious, air-tight wrapper and sterilizing it by exposure to gamma irradiation.

Most preferably the air-tight wrapper or packages used according to the present invention are substantially resealable after initial use of the moist cotton fabric in order to maintain the fabric moist for possible reuse even though the fabric is no longer sterile after its initial exposure to the air. Of course, the moist woven cotton fabric must be laundered or discarded after certain initial uses, or can be retained foe reuse in cases where the initial use is not destructive thereof. For example, moist woven cotton fabric towelette might be stored in the glove compartment of an automobile and reused several times for the removal of casual dirt from the hands, or to clean the windshield, steering wheel or other automobile parts until it becomes so soiled as to require disposal or laundering.

The resealable wrapper or package may be of any conventional type including a zip-lock plastic envelope, a plastic wrapper having a reusable adhesive flap, a relatively thick plastic film-metal foil laminate capable of forming and holding an air-impervious fold, or other similar wrapper or package.

The preferred woven cotton fabric towelettes used according to the present invention are 100% cotton terry towelettes with over lock stitch bordering, from about 144 to 196 loops per square inch or one of both surfaces and having a dry weight of from 0.1 to 0.2 grams per square inch. The size of the towelette may vary between about 4 to 10 inches along each edge, with a preferred dimension being a 7 inch by 7 inch square towelette. Terry pile fabrics are preferred for absorbency and cleaning ability. However, other woven cotton fabrics of different weights can be used. While woven cotton fabrics such as terry cotton are more expensive than conventional non-woven paper and/or fiber towelettes, woven cotton fabric towelettes have substantially preferred properties of absorbency, body and texture, resistance to tearing or decomposing under the effects of scrubbing use and natural feel, similar to any ordinary face cloth. Moreover, the additional cost can be offset by the laundering of the present towelettes, if desired, to render them capable of subsequent reuse in either moist or dry condition. In moist condition they can be reinserted into their original packages and resealed, although they must be reused in the immediate future since they are no longer sterile.

The preferred aqueous moistening liquid is pure water such as natural spring water since such water is substantiall free of additives such as chlorides, fluorides, etc., and substantially free of pollutants, bacteria and other microgranisms and impurites. Even though the present products are sterilized in packaged form, it is important to some users that the moist towelettes of the present invention be free of unnatural impurities as well as being sterile, i.e,. free of living microorganisms and incapable of growing such microorganisms so long as the package remains unopened.

According to another embodiment of this invention, the aqueous moistening liquid can contain minor amounts of water-soluble additives such as alcohols for skin freshening, iodine solution for antiseptic purposes, fragrances, glycerin or lemon oil or other skin smoothness agent, etc. However, such additives preferably should not exceed about 10% of the total weight of the aqueous solution.

The present packaged towelettes preferably are produced by inserting a dry woven fabric towelette, such as a 7"×7" terry cotton towelette which is folded into a four ply, 3½"×3½" size, into a hermetically sealable envelope, one end of which is open. A suitable envelope is one formed from a laminate of aluminum foil, 0.0007" in thickness, cellophane film, low density polyethylene film, and ethylene acrylic acid copolymer bonding the cellophane film to the exterior surface of the aluminum foil and bonding the heat-sealing polyethylene film to the interior surface of the aluminum foil. Each envelope is formed by superposing two sheets of such laminate having approximate outer dimensions of 4-7/8"×5⅛", with the polyethylene film side of each sheet in contact, and applying peripheral heat and pressure along a ¼" margin around three sides to leave one 5⅛" side unsealed.

The dry, folded towelette, as clean and sterile as possible, is fully inserted into the open end of the envelope and a predetermined volume of the aqueous composition is injected into the open end of the envelope to saturate the towelette. A preferred volume for 7"×7" terry cotton towelettes is approximately 17.5 milliliters which is slightly less than 0.6 ounce of pure water. Thereafter, the envelope is compressed lightly to expel excess air. The water remains absorbed by the towelette. Then the open end of the envelope is sealed by pressure and heat in the same manner as the other three sides so that the towelette is hermetically sealed to prevent the escape or evaporation of the aqueous composition therefrom and to prevent the entry of air of other external impurities.

Finally, the packaged towelettes are sterilized by irradiation in order to kill any bacteria or microorganisms which are present within the package and prevent the growth thereof, a problem which is normally encountered to a great extent with cotton fabric which is moist with aqueous compositions. Preferably, sterilization is accomplished by exposing the sealed packages to gamma radiation from radioactive cobalt 60 in a dosage of from about 0.5 Mrad to about 2.0 Mrad.

The sterilized packaged towelettes of the present invention have an indefinite shelf life of several years provided that the package remains hermetically sealed. Even after packages of the aforementioned aluminum foil type are opened by carefully tearing along one edge and withdrawing the towelette for use, the moist towelette can be reinserted and the package can be resealed by folding across the opened end to maintain the towelette moist for several weeks since the aluminum foil is sufficiently thick to retain its folded condition.

As mentioned supra, the package of the present woven fabric towelettes may be a reclosable zip-lock plastic film envelope of suitable size or a plastic film package having a resealable adhesive closure, of the type conventionally-used for thin paper towelettes moistened with conventional compositions.

It is to be understood that the above described embodiments of the invention are illustrative only and that modifications throughout may occur to those skilled in the art. Accordingly, this invention is not to be regarded as limited to the embodiments disclosed herein, but is to be limited as defined by the appended claims.

What is claimed is:

1. Method for providing moist towelettes which are sterile, durable, suitable for repeated reuse and capable of laundering for subsequent reuse in either moist or dry condition, said method comprising forming an absorbent woven cotton cloth towelette, folding said towelette into a multi-ply reduced size, inserting said folded towelette into package which is capable of being sealed and rendered water-impervious, injecting a sufficient volume of an aqueous composition into said package to impregnate said towelette therewith, sealing said package to render it water-impervious and exposing said sealed package to sufficient radiation to sterilize said impregnated towelette and maintain it sterile for so long as said package remains sealed, said woven cotton fabric towelette being capable of being laundered for subsequent reuse in either moist or dry condition.

2. Method according to claim 1 in which said package has resealable opening means to permit said impregnated towelette to be removed from the package, used and reinserted and resealed to maintain it in moist condition for reuse.

3. Method according to claim 1 in which said woven cotton cloth comprises terry cotton.

4. Method according to claim 1 in which said package comprises a laminate of a heat-fusible plastic film and a metallic foil and said package is sealed by heat and pressure.

5. Method according to claim 1 in which said package is sterilized by exposure to gamma radiation.

6. Method according to claim 1 in which said aqueous composition comprises pure water.

7. A package containing a moist, sterile, durable woven cotton cloth towelette which is impregnated with an aqueous composition, said package being water-impervious and resealable to permit said woven cotton cloth to remain moist for reuse until it becomes excessively soiled, said impregnated woven cotton cloth being sterilized by exposure to radiation while initially sealed within said package, and being launderable for subsequent reuse after it becomes soiled.

8. A package according to claim 7 in which said woven cotton cloth comprises terry cloth.

9. A package according to claim 7 in which said aqueous composition comprises pure water.

10. A package according to claim 7 comprising a laminate of an interior heat-fusible plastic film and a metallic foil, said plastic film being fused to itself to render the package water-impervious.

* * * * *